United States Patent [19]

Lommi et al.

[11] Patent Number: 5,079,011

[45] Date of Patent: Jan. 7, 1992

[54] METHOD USING IMMOBILIZED YEAST TO PRODUCE ETHANOL AND ALCOHOLIC BEVERAGES

[75] Inventors: Heikki Lommi, Kantivik; Juha Ahvenainen, Helsinki, both of Finland

[73] Assignee: Cultor, Ltd., Finland

[21] Appl. No.: 249,898

[22] Filed: Sep. 27, 1988

[51] Int. Cl.$^5$ ............................ C12P 7/06; C12P 7/08
[52] U.S. Cl. ............................. 426/11; 426/13; 426/14; 426/15; 435/161; 435/162; 435/179
[58] Field of Search .................. 426/11, 13-15; 435/161, 162, 179

[56] References Cited

U.S. PATENT DOCUMENTS

| | | | |
|---|---|---|---|
| 4,350,765 | 9/1982 | Chibata et al. | 435/162 |
| 4,355,108 | 10/1982 | Gaddy et al. | 435/165 |
| 4,355,117 | 10/1982 | Antrim et al. | 435/179 |
| 4,459,312 | 7/1984 | Hartmeier | 426/13 |
| 4,546,081 | 10/1985 | Yamada et al. | 435/161 |
| 4,680,263 | 7/1987 | Yamada et al. | 435/162 |
| 4,698,224 | 10/1987 | Nakanishi et al. | 426/11 |
| 4,698,224 | 10/1987 | Nakanishi et al. | 435/162 |
| 4,822,534 | 4/1989 | Lencki et al. | 435/178 |
| 4,822,737 | 4/1989 | Saida | 435/162 |
| 4,915,959 | 4/1990 | Pajunen et al. | 426/11 |

FOREIGN PATENT DOCUMENTS 180404 5/1986 European Pat. Off. .

OTHER PUBLICATIONS

European Brewery Convention Congress, Madrid 1987, pp. 441-448, IRL Press Oxford G.B., Pajunen et al.

CA.71:278448 (1969) Kurozumi et al., Biochim Biophys Acta (1969) 177(3) 6535.

Joung et al., "Applied Biochem & biotechnology", vol. 14, 1987, pp. 259-275.

*Primary Examiner*—Herbert J. Lilling
*Attorney, Agent, or Firm*—Kenyon & Kenyon

[57] ABSTRACT

According to the invention, yeast cells are immobilized on a substantially noncompressible carrier having anion exchange properties. The immobilized yeast can then be used to ferment a sugar-containing substrate. The noncompressibility enables the system to be sterilized and to operate under pressure. A preferred example of the carrier is granular DEAE cellulose.

21 Claims, 1 Drawing Sheet

METHOD USING IMMOBILIZED YEAST TO PRODUCE ETHANOL AND ALCOHOLIC BEVERAGES

This invention relates to production of ethanol and more specifically to production of alcoholic beverages using immobilized yeast which is bound to a regenerable carrier material. Yeast immobilization can be carried out in the fermentation reactor itself thus minimizing the risk of contamination during the immobilization.

BACKGROUND OF THE INVENTION

Fermentation is an art that began before recorded history. It was, however, only in 1866 that Pasteur published his works on wine fermentation, analyzed the reasons for spoilage, and prescribed an appropriate treatment for wine making.

Traditionally the fermentation takes place with the wild yeasts that occur on all fruits and berries. Fermentation with pure culture yeasts is used more often today in order to consistently produce good quality wines. All these general aspects of wine making and characterizations of the yeasts are presented in "Biotechnology" edited by H-J Rehm and G Reed Vol. Food and Feed Production with Micro-organisms, Verlag Chemie or in Prescott & Dunn's Industrial Microbiology 4th edition, chapter 9, 1982 edited by G. Reed, the disclosure of which in incorporated herein by reference.

Traditional batch fermentation is time consuming. A typical time for the alcohol fermentation in wine making normally requires at least 20–50 days. Although a continuous process with suspended yeast might be thought to speed this process it is difficult to operate and maintain free from microbial contamination. Moreover, to speed up the fermentation rate, the yeast cell concentration in the fermenting must should be increased while on the other hand the ethanol inhibition should be minimized. In a batch fermentation, for example with apple juice, the yeast cell concentration is $1-2 \times 10^8$ cells/ml of must/broth.

A higher yeast cell concentration can, for example, be arranged by immobilizing the yeast on a suitable carrier packed in a column. When the fermenting must is passed through the column packed with immobilized yeast, the number of yeast cells in contact with the volume of must in the reactor is greatly increased. This greater contact area results in a faster fermentation. The column reactor also reduces the ethanol inhibition since the ethanol containing product is continuously removed from the yeast bed. This reduction is greater as an ideal plug flow situation is approached.

It is known that yeast cells can be entrapped in calcium alginate and the resulting immobilized yeast can be used for fast fermentations. Numerous literature references describe this technique as it is applied usually in laboratory scale. Some efforts, however, have also been made to commercialize this technique. One of the best known is probably that of Kyowa Hakko in Japan, where alginate immobilized yeast is used for feed ethanol production.

For commercial scale operations, a major difficulty with alginate entrapment is the manner in which the particles are formed. It must be carried out at the production site where a yeast slurry and a solution of sodium algonate are mixed together. When this mixture is then fed into a calcium-salt solution, the alginate precipitates and at the same time occludes the yeast cells within the precipitated particles. The particles usually are in the form of droplets/beads.

A process plant that utilizes alginate entrapped yeast must have specially designed equipment just to produce these beads. Furthermore, there is a potential risk for contaminating the yeast with wild microorganisms. This is especially critical when production of an alcoholic beverage flavor is important (e.g., beer, wine, cider and similar kinds of products). For technical/fuel ethanol production the criteria of contamination is not as important as in the consumables although it does affect the productivity.

A second major difficulty for alginate beads used on a commercial scale is in the physical strength of the beads. The beads are soft and easily compressible. Operating large fermentation columns can be a problem and fast downflow process streams are difficult to handle. On the other hand, a typical upflow mode in fermentation greatly wears the beads. Also, to run a reactor downflow under pressure with compressible material is virtually impossible.

A third difficulty with entrapment is the diffusion limitations which slow down the accessibility of the substrate in contact with the yeast inside the bead.

Finally, if the system becomes contaminated or otherwise disturbed so that a continuous operation must be discontinued, the whole lot of column material (alginate together with the yeast) must be discarded. No reuse is possible.

Therefore, it is an object of the present invention to develop a method for continuous column fermentation that does not require on-site formation of the column material. Another object is to develop a method that eliminates sources of contamination. Yet another object is to develop a method of this type that can withstand pressure. Still another object of this invention is to develop a method where the carrier material can be regenerated and reused. Further objects include development of processes that produce alcohol at reasonably rapid rates such as at least a minimum of about 1 bed volume of about 5 percent alcohol per day.

SUMMARY OF THE INVENTION

These and other objects are achieved by the present invention which is directed to a method for the primary production of an ethanolic product. According to this method, an aqueous substrate containing a dissolved yeast-fermentable carbohydrate is contacted with yeast immobilized upon a carrier having anionic exchange properties. The contact can be preferably accomplished by passing the aqueous substrate through a packed bed reactor of the yeast immobilized upon the carrier. However, it may also be accomplished by use of the immobilized yeast in a fluidized bed reactor.

The yeast-carrier combination is comprised of yeast bound to the surfaces of the porous carrier. The carrier is substantially non-compressible. It is composed of a continuous porous matrix, or alternatively, of dimpled or reticulated, porous particles. The matrix or particles, in turn, are composed of individual microparticles or microfibers. This carrier structure provides a maximal surface area for carrying yeast cells. The resulting high number of yeast cells per unit volume of carrier makes rapid fermentation possible.

The particulate or matrix character of the carrier is produced by loosely binding, felting, weaving, gluing or agglomerating (hereinafter binding) the microparticles or microfibers together. The binding is accomplished by establishing chemical, adherent or mechanical links at some of the contact points between the individual microparticles or microfibers. Chemical binding is accomplished by causing a chemical cross-linking reaction at these points. Adherent ending is accomplished by agglomerating or gluing the microfibers or microparticles together through the use of an additional ingredient such as a thermoplastic resin. Mechanical binding is accomplished by entangling or knotting the fibers at the contact points or by joining the particles by meshing their surfaces together. In its final form, the matrix will comprise a continuous structure throughout the reactor, much like cotton fluff or filter paper packed into a tube. Also, in their final form, the particles will be discrete and individual.

The microfibers or microparticles are composed of any anion exchange substance that can be formed into the desired, rough-surfaced microfibers or microparticles. These substances include native or regenerated cellulose or rayon that is derivatized to provide anion exchange character; synthetic anion exchange resins such as phenolformaldehyde resins, and agarose or dextrin based anion exchange resins. The preferred carrier is a porous, particulate anion exchange resin derived from cellulose or rayon that has been chemically modified to provide anion exchange character. Especially preferred embodiments include microfibers or microparticles of diethylaminoethylene substituted cellulose, adherently bound by agglomeration with polystyrene.

It is believed that the electric forces established between the positively charged resin and the negatively charged yeast cells are primarily responsible for the binding of yeast cells to the surfaces of the resin. This binding minimizes substantial leaching of the yeast yet permits intimate contact between the yeast and the aqueous medium.

The aqueous substrate used as a starting material is composed at least of water and a fermentable carbohydrate such as hydrolyzed starch, sucrose, glucose, fructose, maltose or maltotriose (lactose and xylose). The concentration of sugar will be sufficient to permit continuous production of alcohol but will be not so high that the fermentive activity of the yeast is completely inhibited.

According to the method of the invention, it is important to control the processing parameter involving carbon dioxide produced by the fermentation. The carbon dioxide can be maintained in the fluid product stream or removed. In a preferred method, a series of columns is employed, the interconnections of which are adapted for removal of gas from the column outlet stream. By maintaining the columns under some pressure, a carbonated product can be produced. If the column interconnection taps are all employed, a product without carbonation will be produced. The column pressure, however, cannot be so high as to substantially diminish the yeast fermentation. Facile routineering can establish this limit which, in general, will be at least about 14 bar.

In addition to pressure, other processing parameters can be varied to affect the output of ethanol and taste of the product. These parameters include column temperature, aqueous substrate feed rate, column residence time, direction of substrate flow in the column (with or against gravity), periodic reversal of flow direction, yeast strain, yeast concentration and yeast nutrients in the aqueous substrate. Suitable ranges for these parameters include a temperature of about 0° to 40° C., feed rate 0.01-10 reactor bed volume (BV)/hour, a residence time of about 0.1-100 h and yeast concentration of about $10^9$ to about $10^{12}$ yeast cells per litre carrier Yeasts such as Saccharomyces or Candida can be used. Generally, these parameters will be adjusted to produce an ethanol concentration of from 0.05 to 15 percent.

In a preferred method of the invention, a slurry of the particulate carrier is first placed in a column and the carrier allowed to settle into a packed column. The carrier is sterilized by a method such as washing with hot caustic. After neutralizing with sterile, dilute acidic solution and rinsing with sterile water, the column is then eluted with a yeast broth so that the yeast becomes attached to and immobilized on the carrier particles. After this pretreatment, the column of yeast is used as described above.

In a further preferred method of the invention, an ethanolic product that is consumable is produced. This product can be wine, sake, an alcoholic fruit, berry or vegetable drink, carbonated versions thereof, beer, or low alcohol version's of the foregoing products.

The aqueous substrate used to produce the consumable product is derived from a source such as a fruit, berry or vegetable juice or extract, a wort, hydrolyzed plant material or an aqueous syrup containing a fermentable sugar derived from a natural or synthetic source. The juice will be a liquid pressed from a fruit, berry or vegetable. The extract will be a liquid produced by combining the fruit, berry or vegetable with water and processing by mashing, cooking, pressing, mixing and the like. The hydrolyzed plant material will be material that is derived from cellulose, hemicellulose and/or starch through a technique such as acid, enzyme or auto-hydrolysis.

Another method of the invention is directed to production of low alcohol beverages such as those containing less than 0.2 percent by volume alcohol. According to this method, the steps practiced and the yeast-carrier material are the same as those of the primary production method. The sugar content and feed rate of aqueous substrate, however, are modified to provide the "low alcohol" production. The feed rate is increased to an extent that decreases the alcohol concentration to the value desired. The sugar concentration is also appropriately adjusted so that the beverage is not overly sweet yet enough sugar is present for fermentation to alcohol.

The invention is further directed to the combination of the carrier and yeast in any form. Preferred forms include that made in situ, as described above, and a dried combination.

The dried combination in aseptic condition can be packaged, transported to a fermentation plant and reconstituted for by immersion in aqueous nutrient. Alternatively, the dried form can be packaged for home use.

DETAILED DESCRIPTION OF PREFERRED EMBODIMENTS

Figure 1:
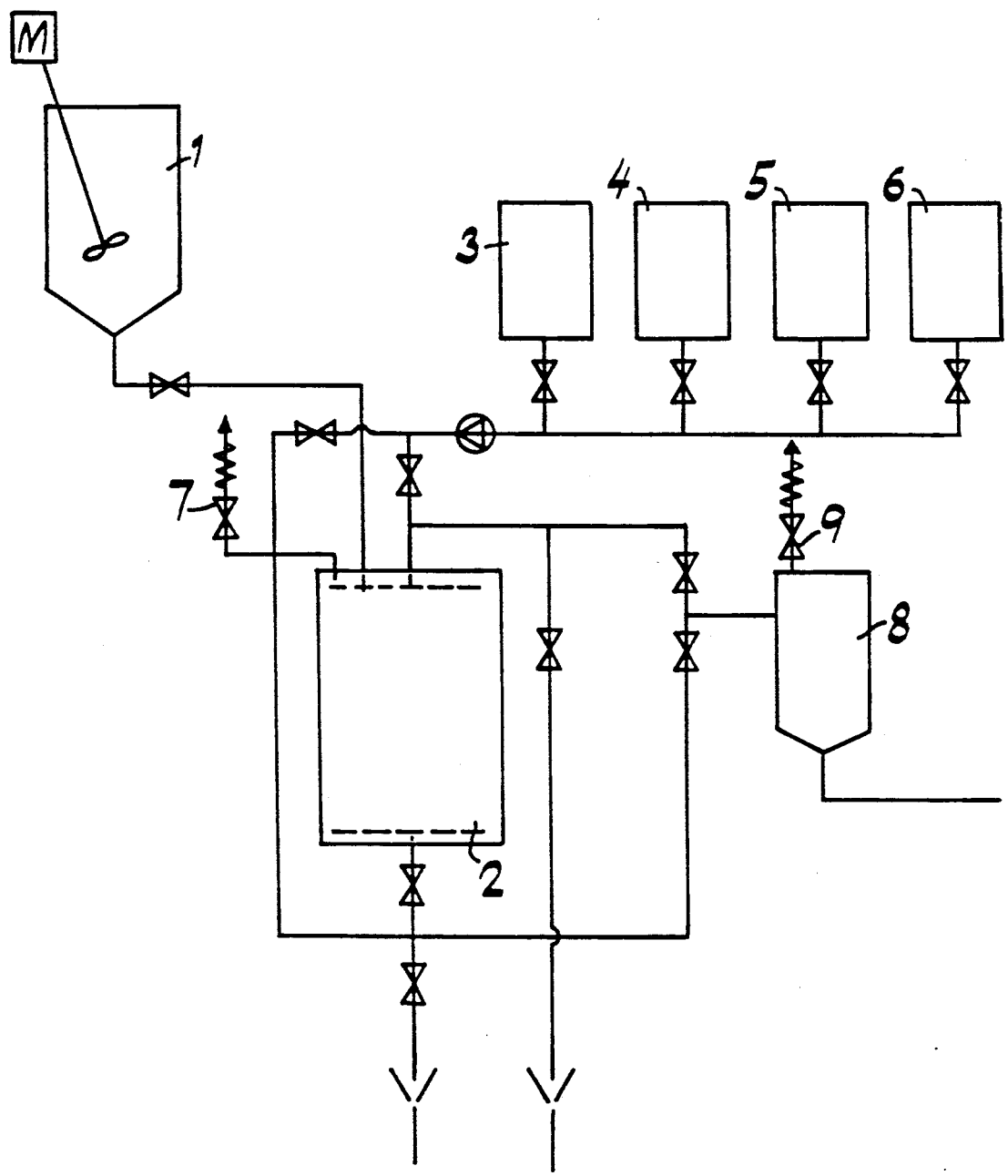
FIG. 1 shows a simplfied flow scheme for preparing the immobilized yeast columns.

The present invention is based upon a yeast-carrier system, described above, that is non-compressible and sterilizable An especially preferred example of a carrier for use in producing the yeast-carrier system is particulate DEAE cellulose (weak anion exchanger) agglomerated with polystyrene. This carrier is commercially available and is well-known for immobilizing enzymes, typically isomerase. (See U.S. Pat. No. 4,355,117 for details regarding this carrier.)

In a preferred process for preparing the yeast-carrier system as depicted in FIG. 1, the dry carrier is hydrated in water and pumped as a slurry into a column reactor. The preferred DEAE cellulose carrier is stable in acid and alkaline media and can withstand a temperature up to 100° C. It can thus be easily sterilized in the column, for example, with hot caustic. Other resins can appropriately be sterilized in similar fashion.

Yeast immobilization onto the carrier is accomplished after sterilization of the carrier. It is carried out by pumping a cultured, active yeast slurry into the reactor. The carrier then adsorbs the yeast. The yeast cells attach to the carrier surfaces as a result of the optimal surface shapes of the carrier. It is rough, reticulated and exists as a continuous or particulate porous matrix. The attachment is believed to result from electrical forces between the anionic exchange groups (positively charged) of the carrier and the negatively charged yeast cell wall.

Preferably, the yeast cells are grown on the carrier to provide a density of between about $10^9$–$10^{12}$ cells per liter of carrier, with a density of about $10^9$ cells being particularly preferred. The density must be sufficient to provide enough enzymatic activity to substantially convert the sugars in the aqueous substrate to ethanol.

The carrier is important in terms of providing an adequate environment for yeast growth and contact with the aqueous substrate. The non-compressible anion exchange carrier, such as agglomerated DEAE-cellulose, has several beneficial qualities compared with soft, gel-like carriers, such as alginate beads. These qualities include fewer mass transfer problems, easier immobilization, faster start-up, easier scale-up, much improved regenerability and a long life-time of the carrier.

In laboratory scale experiments a gel-like carrier, i.e., alginate beads, and a preferred carrier of the invention, i.e., DEAE-cellulose granules, have been compared. The carrier made from DEAE-cellulose was more facile to use for ethanol production and with many substrates had a more desirable production capacity These factors suggest a better contact between yeast and aqueous substrate during treatment.

Although not intended as a limitation of the invention, it is believed that the mode of interaction of the immobilized yeast and the carrier according to the invention may explain the increased yield. Electron micrographs show that in the alginate beads, the yeast grows in colonies, some of which grow through the alginate layer to the bead surface. The yeast colonies presumably act as the "active sites" in the alginate beads. The microphotographs show that the DEAE-cellulose granules are porous, reticulated matrices of microfibers. This structure permits the aqueous substrate to reach yeast cells growing inside the granules. Thus, the yeast grows rather loosely and separately in the internal and external pockets of the microfibers and these individual cells act as "active fermentation sites" in the column. Accordingly, more yeast cells per unit carrier surface area are available for fermentation when the carrier of the invention is used.

The mechanism of the yeast cell immobilization onto the surface of the carrier, such as granular DEAE cellulose, offers many benefits. First, the yeast cells are substantially all on the surface of the carrier. Thus, the cells act as if they were freely suspended in a solution.

Second, there are no substantial diffusion limitations and the fermentable fluid substrate can freely come into contact with the yeast. Also the nutrients that the yeast needs for life are available without hindrance from the need to permeate into the interior of the carrier particles.

Third, the carrier properties according to the invention also permit easy start-up and regeneration because the yeast cell immobilization can take place in situ within the column. This procedure lowers the risk of contamination and improves the conditions of the system as a whole. In addition, the column can be easily regenerated which is an important economic feature. Regeneration is sometimes expedient because of chemical impurities or contamination from the aqueous, microbial contamination or from mutations of the immobilization yeast itself. To regenerate a column reactor made from a carrier such as DEAE cellulose, for example, the spent column can be washed and sterilized with a hot caustic solution or with another sterilizing medium such as an organic agent in water and the like. After washing and neutralization, the carrier is ready for repitching and reimmobilization. In pilot scale set-ups, such a column has been utilized for at least thirteen weeks without need for regeneration. In lab scale, a similar column has been utilized for about 30 weeks.

In general, the entire reactor system, including the carrier, can be sterilized with the above-mentioned treatment. When an aseptically cultured yeast is then pumped or eluted through the carrier bed, the risk of contaminating the yeast/carrier with wild strains or bacteria will be minimal. When the yeast is attached to the column (a suitable charge is about $10^9$ to $10^{12}$ yeast cells/liter carrier) the column can be further conditioned by slowly pumping a nutrient solution such as an aqueous medium of ammonium phosphate and sugar through the reactor for approximately one day. This process causes the yeast to flourish to a maximum density.

As is generally true of all yeast-carrier systems used according to the invention, one of the preferred carrier embodiments, granulated DEAE cellulose, is non-compressible (non-swelling). This property allows much variation as to how the fermentation can be conducted.

Under normal atmospheric pressure, the reactor/continuous fermenter may be operated as follows. The substrate is fed in from the bottom of the reactor and the $CO_2$, which is formed during the fermentation, is freely allowed to evolve from the carrier bed. With this technique, however, an ideal plug flow situation cannot be reached ($CO_2$ bubbles always disturb the bed) and backmixing causes ethanol inhibition and thus lower productivity.

The non-compressible carrier system of the present invention can also be operated under pressure in order to maintain the carbon dioxide in a dissolved state. The column can then also be run in a downflow condition and in this packed bed system, an ideal plug flow is reached.

Several pressurized columns may also be run in series to avoid high pressure. The series arrangement is especially useful if a large concentration of alcohol in the final product is desired. This method enables the operation in a downflow mode without the harmful release of carbon dioxide which could disrupt the packed character of the column i.e. cause channelling. Between the columns, carbon dioxide is separated from the stream. The reactor size can also be kept smaller as no extra fluidization and carbon dioxide-separation space is needed.

Basically any fermentable fluid substrate can be used as feed material for production of the ethanolic product provided that any particulate impurities are filtered out before feeding into the immobilized yeast column. Examples of typical substrates would be:
 (i) wort
 (ii) fruit juice,
 (iii) berry juice
 (iv) sugar syrup
 (v) starch syrup
 (vi) any hydrolysate out of plant material
 (vii) sugar syrups flavored by any fruit, berry, malt or similar extracts
 (viii) any aqueous substrate that is used in beer, wine or liquor production A typical total sugar concentration would be 100-250 g/L including both original and added sugars depending on the basic raw material. The yeast nutrients (including sources of phosphorus, nitrogen etc.) need to be balanced unless they are favorable in the original raw material. The sugar concentration can, of course, be varied widely depending on how much alcohol and how much sweetness the end product is expected to have. It may also contain natural flavors, oils and the like. The sugar will be present at a concentration of from at least about 1 percent by weight to an amount that will inhibit fermentation function (e.g., about 30 to 40 percent by weight), preferably about 4 to 25 percent by weight relative to the total weight of the medium.

The flow rate of the aqueous substrate through the column is an important parameter because the ethanol production capacity is dependent on the flow rate. It has also been shown that the flow rate determines the number of yeast cells which remain bound in the carrier. With high flow rates, the yeast cell outflow is increased; consequently ethanol production may also be dependent on the cell number bound in the immobilized system, and not only on the throughput rate of the substrate. If the flow rate is too high, the ethanol production is incomplete and/or inadequate; by controlling the flow rate, the ethanol concentration can be controlled, typically by seeking a concentration which is from about 0.05 percent to about 15 percent by volume relative to the total volume of the aqueous substrate. By adjusting the flow rate, the fermenter can obtain an ethanol concentration within this range.

The amount of yeast cells which remain bound to the carrier material appears to be relatively stable at low flow rates, suggesting that yeast growth and leaching of the cells are balanced. With higher flow rates leaching increases but the cell number returns back to the normal level again when the flow rate is decreased. The flow rate should be high enough to enable the leaching of dead cells in order to avoid autolysis. During the operation of the immobilized yeast column, the yeast is maintained viable by fermentable sugars in the aqueous substrate.

The immobilized yeast column reactor can be pressurized as discussed above. The operation pressure should be high enough to keep the carbon dioxide soluble in the column and to avoid the possible channeling of the $CO_2$ bubbles through the immobilized yeast column. Typical measure is 14 bar.

A suitable temperature is that used in traditional batch fermentation processes. It will range from about 0 to about 40° C., preferably about 10° to about 35° C. This temperature can be maintained either by warming the columns with heating jackets or maintaining the columns in an environmentally controlled room, or by cooling. Of course, the yeast also develops a certain degree of heat that also can be used to advantage. The pressure is chosen according to the operation temperature.

Following fermentation, the eluted ethanolic product is cooled down to the storage temperature and collected into a buffer tank for the conventional post-fermentation treatment, e.g., filtering, pasteurization and packaging.

The ethanol production system described above is a faster and more convenient system than traditional fermentation processes and produces a product with acceptable taste equivalent to the taste resulting from conventional fermentation processes. The time needed for fermentation is reduced from weeks to a matter of hours by the present invention which, along with the continuous nature of the process, provides a vast potential for time and money savings in commercial alcohol or alcoholic beverages production.

The following examples further illustrate many aspects of this invention. The examples, however, are not meant to stand as limitations or characterizations of the invention as it has been fully characterized in the foregoing text.

Preparation of Column Reactor

Granular DEAE-cellulose (GDC) manufactured according to U.S. Pat. No. 4,355,117 by Finnish Sugar Co. Ltd. of particle size 315-840 m or 470-840 m was used as a carrier for the examples 1-3. In all the experiments the carrier was filled, sterilized and yeast immobilized thereon according to the following procedure for handling GDC:

Procedure for Preparing GDC Column and Immobilizing Yeast

With reference to FIG. 1, the hydration vessel (1) is first filled half with water. The mixer is started and dry carrier (GDC) is transferred to the vessel (1). When the hydration is completed (about 5 hours) the immobilized yeast reactor (2) is filled half with water and the carrier water slurry from the hydration vessel (1) is transferred to the reactor (2). In order to maintain the water level in the reactor the bottom valve on the reactor is adjusted so that inlet and outlet flows from the reactor are about the same. The carrier in the reactor is then sterilized with dilute caustic (3) by pumping it through the reactor (2). The carrier bed is then rinsed with water and neutralized by pumping a suitable dilute acid (4) through the carrier bed in the reactor (2) and finally the carrier is rinsed with sterile water.

A yeast slurry is made up in the vessel (5). The yeast slurry is then pumped through the carrier bed in about 1-4 hours and the yeast will bind itself to the carrier. The yeast is now immobilized onto the carrier and the reactor (2) is basically ready for fermentation.

The substrate from vessel (6) is then pumped through the reactor either through the bottom or top inlet. By adjusting the flow rate one can control the level of fermentation. Slow flow rate (about 1BV/day) means long contact time between the carrier and the substrate and thus high alcohol levels. Faster flow again lowers the alcohol level. The reactor can be run under atmospheric pressure feeding from the bottom inlet let the carbon dioxide separated from the system freely through a separation port (7). The product is collected to a receiving vessel (8) from where it is further processed through filtration etc. before final bottling.

When the system is operated under pressure, the substrate (6) is fed from the top inlet in order to keep the carrier bed in packed form and thus reach a plug flow. The fermentation rate is controlled in such a manner (by flow rate) that the applied pressure is high enough to maintain the formed carbon dioxide dissolved. The pressure is released through valve (9) on the receiving vessel unless the final product is intended to contain carbon dioxide. In order to keep pressure and dissolved carbon dioxide in reasonable limits, it is advisable to have two or more similar reactors (2) in series and release the excess carbon dioxide between each reactor.

EXAMPLE 1

Wine

Apple juice has been used as substrate in four different column reactor fermentation experiments.

In the first two experiments ($A_1$ and $A_2$) the yeast was normally cultured as it is done for batch fermentations and the carrier beds of about 500 ml each were prepared with an amount of yeast cells as described above.

Immediately after the yeast had been rinsed through the carrier bed in the two columns (diameter - 50 mm and height - 250 - 300 mm) the substrate feed was started with a flow rate of 1 BV/day. The substrate was pasteurized apple juice where 1 of ammonium phosphate was added as yeast nutrient. The total sugar concentration was adjusted to 220 g/l by adding sugar to the apple juice. The fermentation started slowly and after 3 weeks the outflowing wine had 4.5-6.5 % of ethanol. The carrier in this experiment had a particle size of 0.315 to 0.840 mm.

Carbon dioxide removal from the column was complicated by the narrow shape of the columns. A column, which was loaded with a carrier of the particle size 0.470-0.840 mm, behaved better as carbon dioxide could more easily percolate out from the carrier/yeast bed. From both columns some GDC was blown out with the carbon dioxide bubbles 50 days operation the flow rate was reduce to about 0.8 BV/day which immediately increased the ethanol level during the following week from 5 % to 7-8 %. After 75 days of operation the nutrients were further increased to 2 g/l but no effect could be seen in the columns $A_1$ or $A_2$.

The third experiment $A_3$ was carried out in column which was wider and shorter. Reason for this was to make carbon dioxide removal easier. When the carrier bed had been sterilized with hot caustic and washed and neutralized with water and sodium-metabisulphite, the yeast immobilization was carried out with substantially higher yeast cell concentration For 500 ml of GDC, 600 ml of yeast slurry was used which contained 150 million cells/ml. The leakage through the column was 5 million cells/ml so the total mobilized amount was $9 \times 10^{10}$ cells. This is equal to $2 \times 10^9$ cells/ml GDC or $5 \times 10^9$ cells/g GDC.

For one day the column was eluted with yeast nutrient solution before beginning with apple juice substrate. The fermentation started rapidly when compared to $A_1$ and $A_2$ and on the second day the ethanol level was already at 8%. The flow rate was 1 BV/day and nutrients 1 g/l juice. Some material was also lost from this column by carbon dioxide reflex.

Reduction of feed rate after 3 weeks caused the alcohol level to raise again. After 1.5 months the nutrient level was raised to 2 g/l which raised the alcohol level further and the system stabilized at about a 10% ethanol level during its third month of operation.

The fourth experiment was carried out in a 8 1 reactor following the same procedure as with $A_3$. The reactor is constructed so that in the outlet line there is also a screen plate to hold back any GDC particles. The system stabilized into a 10% alcohol level within a week. A portion of the product from the 8 1 reactor was further fed to a second 500 ml column to increase the level of ethanol.

All the experiments were carried out in room temperature 20°-23° C. When the second reactor is operated under pressure high enough to keep the carbon dioxide dissolved the product is a sparkling champagne type wine, which if bottled under the same pressure as it is fermented makes the secondary, fermentation unnecessary in the bottles and thus makes the 'champagne' process less complicated.

EXAMPLE 2

Beer

In this example, primary beer fermentation can be carried out in an immobilized yeast column.

The column preparation and yeast immobilization can be carried out following the procedure described in the foregoing section on the reactor preparation. A 500 ml carrier bed can be packed in a glass column which is wider in the upper end in order to ease the carbon dioxide separation. The wort can be fed into the bottom of the fermentation column. The preferred yeast cell concentration can be adjusted to be $10^9$ cells/g GDC.

Traditional wort for lager beer brewing can be used as a feed material for this experiment. The wort can be produced from 18 kg of barley malt (pilsner type) which will give a final volume of 100 l of finished wort (12.0 P). The mixture of water and malt grist can be mashed in one vessel by programmed infusion method with rests at temperature 48° C. for 15 minutes, 63° C. for 30 minutes, 72° C. for 20 minutes and 78° C. at the end of mashing.

The wort can be clarified in a lautertun and rinsed twice with 78° C. water. The wort can be boiled in a wort kettle for about 90 minutes. Hop pellets can be added at the beginning of boiling (total amount of alpha acids is about 10g). Any precipitation formed during boiling can be separated in a whirlpool. The clarified wort can be cooled in a plate heat exchanger from 100° C. to 10° C.

The preferred composition of the wort that is sought

| Original extract | 12.0 | ° Plato |
|---|---|---|
| Color | 10.0 | ° EBC |
| Bitterness | 25 | EBU |
| pH | 5.3 | |
| Apparent attenuation rate | 85% | |
| The composition of the wort, however, can vary as follows: | | |
| Original extract | 6-18 | ° Plato |
| pH | 4.5-5.5 | |
| Apparent attenuation rate | 65-100% | |

Fermentation of the wort in the reactor column can be started slowly. After one week's operation, the rate will be capable of producing an acceptable beer at less than one bed volume/day feed rate. The column behavior was similar to that of the wine reactors $A_1$ and $A_2$ in Example 1.

Example 3
Sake

In this example low alcohol sake (Japanese rice wine) was produced. The column was prepared and the yeast was again immobilized following the procedure set forth in the foregoing section on reactor preparation.

To make the substrate, the rice was first liquefied by steaming and hydrolyzing with alpha-amylase and amyloglucosidase. The resulting hydrolysate was filtered in order to remove all mechanical impurities and unhydrolyzed residues. The substrate was finally diluted so that the glucose concentration was 23% when it was fed into the column. The column had a carrier volume of about 500 ml. Column diameter was 70 mm and diameter to height ratio of carrier about 1:2. Comparison was carried out with Ca-alginate entrapped yeast. The feed rates, parameters and results for both fermentations are given in the following table.

| Support | Result GDC Reactor | Ca-alginate Reactor |
| --- | --- | --- |
| Fermentation period (day) | 15 | 25 |
| Temperature | 15–20 | 15–20 |
| Mean of ethanol (v/v %) | 9.99 | 13.6 |
| Mean of flow rate (BV/h) | 0.069 | 0.099 |
| Productivity (g/h/1-support) | 5.44 | 10.62 |

EXAMPLE 4
Low-Alcohol Beverage

The production of a traditional Scandinavian low-alcohol beverage in an immobilized yeast system is described in this example.

By regulating the feed rate in the fermentation reactor column, the fermentation rate can be controlled and the required flavor and alcohol content in the product can be achieved.

The column preparation and yeast immobilization can be carried out following the procedure described in the foregoing section on reactor preparation. The yeast cell concentration is adapted to provide $10_9$ cells/g GDC.

The aqueous substrate for fermentation can be formulated as follows:

| | |
| --- | --- |
| Crystal (white) sugar | 500 g |
| Honey | 125 g |
| Soft brown sugar | 625 g |
| 2 lemons' juice | |
| Water | 10 l |

A 500 ml carrier bed in a glass column can be eluted from the bottom with the substrate. The feed rate at the beginning preferably may be one bed volume per 5–10 h and after stabilization of fermentation the feed rate can be regulated between one BV/1–5 h depending on the alcohol content and sweetness desired in the product. The alcohol content can vary between 0.2–2.0% w/w in the beverage To maintain the viability of yeast, small amounts of ammonium phosphate (10–100 ppm) can be added as a nutrient.

The production can be carried out at room temperature with the parameters described above. Immobilized reactor can also be operated under pressure at lower temperature. Then the carbon dioxide formed is dissolved and final addition of carbon dioxide can be avoided.

In addition to the foregoing substrate other raw materials can also be used as substrates. All contain fermentable sugars, e.g., malt, fruits and berries. The flavor of the final product will depend on raw material, sugar concentration and fermentation rate.

EXAMPLE 5
Demonstration of Yeast Immobilization On Several Carriers

A brewer's yeast from the "Collection of Industrial Micro-Organisms at the Technical Research Center of Finland" (Collection No. A-75050) was immobilized on two resins with anion exchange functionality.

The resins were: Granulated DEAE cellulose trademarked as SPEZYME GDC 220 and a synthetic anion exchange resin having the trademark DUOLITE A 568.

The immobilizations were performed according to the following procedure:

The yeast was incubated for 48 hours in a malt extract broth at 30° C. The resin was sterilized by washing with 1 M NaOH, buffered to pH 5.0–5.1 and washed with sterile water. 10g dry weight of the resin was flushed in a 20 mm i.d. glass column equipped with a glass sinter bottom plate. 100 ml of the yeast suspension was passed by gravity through the column at an approximate rate of 3 bed volumes/hour, after which the column was washed with 100 ml of sterile water.

The cell concentration of the yeast suspension before and after the immobilization was determined by an agar plate count. From the difference, the number of immobilized cells was calculated. The results as immobilized cells per gram of resin were as follows:

| Resin | Yeast | Offered | Immobilized |
| --- | --- | --- | --- |
| SPEZYME ® | A-75050 | $2,3 \times 10^8$ | $2,1 \times 10^8$ |
| DUOLITE ® | A-75050 | $2,3 \times 10^8$ | $2,2 \times 10^8$ |

What is claimed is:

1. A method of producing an ethanolic product in a primary fermentation comprising:
   obtaining a reactor loaded with an aqueous mixture of a substantially noncompressible positively charged carrier having anion exchange properties;
   eluting the loaded reactor with an aqueous mixture of yeast broth to cause the yeast to become immobilized through electrostatic forces on the carrier;
   passing an aqueous substrate containing a fermentable sugar through the reactor containing immobilized yeast cells to produce the ethanolic product.

2. A method for producing an ethanolic product in a primary fermentation comprising:
   loading a reactor with an aqueous mixture of a substantially noncompressible positively charged carrier having anion exchange properties, to produce a loaded reactor;
   sterilizing the loaded reactor;

eluting the loaded reactor with a yeast broth to cause the yeast to become immobilized through electrostatic forces on the carrier;

passing an aqueous substrate containing a fermentable sugar through the reactor containing immobilized yeast to produce the ethanolic product.

3. A method according to claim 2 further comprising recovering the eluant from the passage of the aqueous substrate through the reactor, thereby producing the ethanolic product.

4. A method according to claim 1 or 2 wherein a consumable ethanolic product is produced and the aqueous substrate is a fruit or vegetable juice, a fruit or vegetable extract, a cereal grain extract or wort, hydrolyzed plant material or a sugar syrup.

5. A method according to claim 1 or 2 wherein the carrier comprises a continuous, porous matrix, or dimpled or reticulated, porous particles, the matrix or particles having a structure formed from a loosely associated plurality of microparticles or microfibers which are chemically, adherently or mechanically bound together at least at some contact points between the individual microparticles or microfibers.

6. A method according to claim 5 wherein the microparticles or microfibers forming the particles are composed of an anion exchange resin.

7. A method according to claim 5 wherein the microparticles or microfibers are composed of an anion exchange resin selected from the group consisting of native or regenerated cellulose derivatized to provide anion exchange character, a -phenol-formaldehyde anion exchange resin, an agarose anion exchange resin and a dextrin anion exchange resin.

8. A method according to claim 7 wherein the anion exchange resin is a native or regenerated cellulose that is derivatized to provide anion exchange character.

9. A method according to claim 7 wherein the microparticles or microfibers are bound together by adherent links.

10. A method according to claim 7 wherein the carrier comprises particles formed from microfibers agglomerated with polystyrene and the anion exchange resin is diethylaminoethylene substituted cellulose.

11. A method according to claim 1 or 2 comprising passing the aqueous substrate through a plurality of reactors connected in series by means for removing gas from the fluid eluted from each reactor.

12. A method according to claim 1 or 2 wherein the aqueous substrate is passed through the reactor at a pressure sufficient to maintain in a dissolved state a substantial portion of the carbon dioxide produced.

13. A method according to claim 12 wherein the pressurization is substantially maintained throughout the production and subsequent steps, thereby producing a carbonated ethanolic product.

14. A method according to claim 1 or 2 wherein industrial ethanol is produced.

15. A method according to claim 1 or 2 wherein consumable ethanol is produced.

16. A method according to claim 1 or 2 wherein the feed rate and reactor residence time are adjusted so as to provide an ethanolic product with an ethanol concentration of from about 0.05 to about 15 percent by volume relative to the total volume of the product.

17. A method according to claim 1 or 2 wherein the flow of aqueous substrate through the reactor is in a direction against the force of gravity.

18. A method according to claim 1 or 2 wherein the flow of aqueous substrate through the reactor is periodically reversed.

19. A method according to claim 1 or 2 wherein the carrier is a continuous matrix or a multitude of dimpled or reticulated, porous particles.

20. A method according to claim 1 or 2 wherein the reactor is a column.

21. A method according to claim 1 or 2 further comprising regenerating the fermentation capacity of a reactor with spent, unproductive yeast by removing the unproductive yeast from the carrier packed within the reactor, sterilizing the packed carrier, and passing new yeast broth through the reactor to cause new yeast cells to become immobilized upon the carrier.

* * * * *

UNITED STATES PATENT AND TRADEMARK OFFICE
CERTIFICATE OF CORRECTION

PATENT NO. : 5,079,011
DATED : January 7, 1992
INVENTOR(S) : Heikki Lommi, Kantivik; and Juha Ahenainen, Helsinki It is certified that error appears in the above-identified patent and that said Letters Patent is hereby corrected as shown below:

Column 1, line 25, delete "Vol" and in place thereof insert --Vol. 5:--

Column 1, line 29, delete "in" and in place thereof insert --is--

Column 4, line 3, delete "109" and in place thereof insert --$10^9$--

Column 4, line 3, delete "1012" and in place thereof insert --$10^{12}$--

Col. 4, lines 50, 51 delete the space between "combination." and "The" to make one paragraph.

Col. 5, lines 51, 52, delete space between "some" and "of" to make one paragraph.

Col. 6, lines 20, 21, delete space between "or" and "with" to make one paragraph.

Column 9, line 46, delete "bubbles 50" and in place thereof insert --bubbles. After--

Col. 9, line 47 delete "reduce" and in place insert --reduced--

Column 9, line 52, delete "column" and in place thereof insert --a column--

Column 9, line 54, delete"Reason: and in place thereof insert --The reason--

UNITED STATES PATENT AND TRADEMARK OFFICE
CERTIFICATE OF CORRECTION

PATENT NO.  : 5,079,011
DATED       : January 7, 1992
INVENTOR(S) : Heikki Lommi, Kantivik; and Juha Ahenainen, Helsinki It is certified that error appears in the above-identified patent and that said Letters Patent is hereby corrected as shown below:

Column 10, line 21, delete "fermented" and in place thereof insert --fermented,--

Column 10, line 21, delete "secondary," and in place thereof insert --secondary--

Column 12, line 9, delete "substrate" and in place thereof insert --substrate,--

Signed and Sealed this

Twenty-fourth Day of August, 1993

Attest:

BRUCE LEHMAN

Attesting Officer    Commissioner of Patents and Trademarks